United States Patent [19]
Dix

[11] Patent Number: 5,819,767
[45] Date of Patent: Oct. 13, 1998

[54] STERILE DENTAL FLOSS SEGMENTS

[76] Inventor: Sean Dix, 145 E. 15th St., Apt. #12A, New York, N.Y. 10003

[21] Appl. No.: 758,262

[22] Filed: Nov. 27, 1996

Related U.S. Application Data

[60] Provisional application No. 60/007,670 Nov. 28, 1995.

[51] Int. Cl.[6] .................................................. A61C 15/00
[52] U.S. Cl. ............................................................ 132/321
[58] Field of Search ..................................... 132/321, 322, 132/323, 324

[56] References Cited

U.S. PATENT DOCUMENTS

| | | | |
|---|---|---|---|
| 3,771,536 | 11/1973 | Dragan | 132/321 |
| 3,802,445 | 4/1974 | Wesley | 132/321 |
| 3,837,351 | 9/1974 | Thornton | 132/321 |
| 3,843,297 | 10/1974 | Espinosa | 425/111 |
| 3,897,795 | 8/1975 | Engel | 132/321 |
| 3,913,596 | 10/1975 | Stuart | 132/321 |
| 3,957,067 | 5/1976 | Ferraro et al. | 132/321 |
| 4,029,113 | 6/1977 | Guyton | 132/321 |
| 4,029,453 | 6/1977 | Campion | 132/325 |
| 4,277,297 | 7/1981 | Thornton | 156/161 |
| 4,807,752 | 2/1989 | Chodorow | 132/323 |
| 4,941,488 | 7/1990 | Marxer et al. | 132/323 |
| 4,986,289 | 1/1991 | McWhorter | 132/323 |
| 5,014,725 | 5/1991 | Patscot et al. | 132/323 |
| 5,021,267 | 6/1991 | Gent | 427/387 |
| 5,024,324 | 6/1991 | Whittaker | 132/324 |
| 5,167,753 | 12/1992 | McCullough | 132/323 |
| 5,220,932 | 6/1993 | Blass | 132/321 |
| 5,582,194 | 12/1996 | Dolan | 132/321 |

*Primary Examiner*—John J. Wilson
*Attorney, Agent, or Firm*—Londa and Traub LLP

[57] ABSTRACT

The present invention relates to sterile dental floss segments having integral tips on the ends thereof, that are compatible for use in dental floss rings and similar type dental floss holders. The dental floss segments have a predetermined length, and are enclosed in a laminated web matrix containing multiple strands of dental floss, which maintains the integrity of the sterility of the dental floss, even after one or more of the strands are removed for use, and also allows for the sterilization of the dental floss strands after laminating the web. The present invention further relates to the method and apparatus to manufacture the sterile web units containing the sterilized dental floss segments with the integral tips on the ends. The method includes unwinding strands of floss in a parallel fashion, such that the strands resemble a web coming off a loom, passing the web through a thread guide to align and adjust the tension in the floss, applying beads of hot melt adhesive material to the exposed sections of the floss to create tips on the ends of the floss, laminating the floss with two layers of sterilizable glassine substrate material, perforating and die-cutting sections of the laminated web across the web at the back hardened beads.

18 Claims, 3 Drawing Sheets

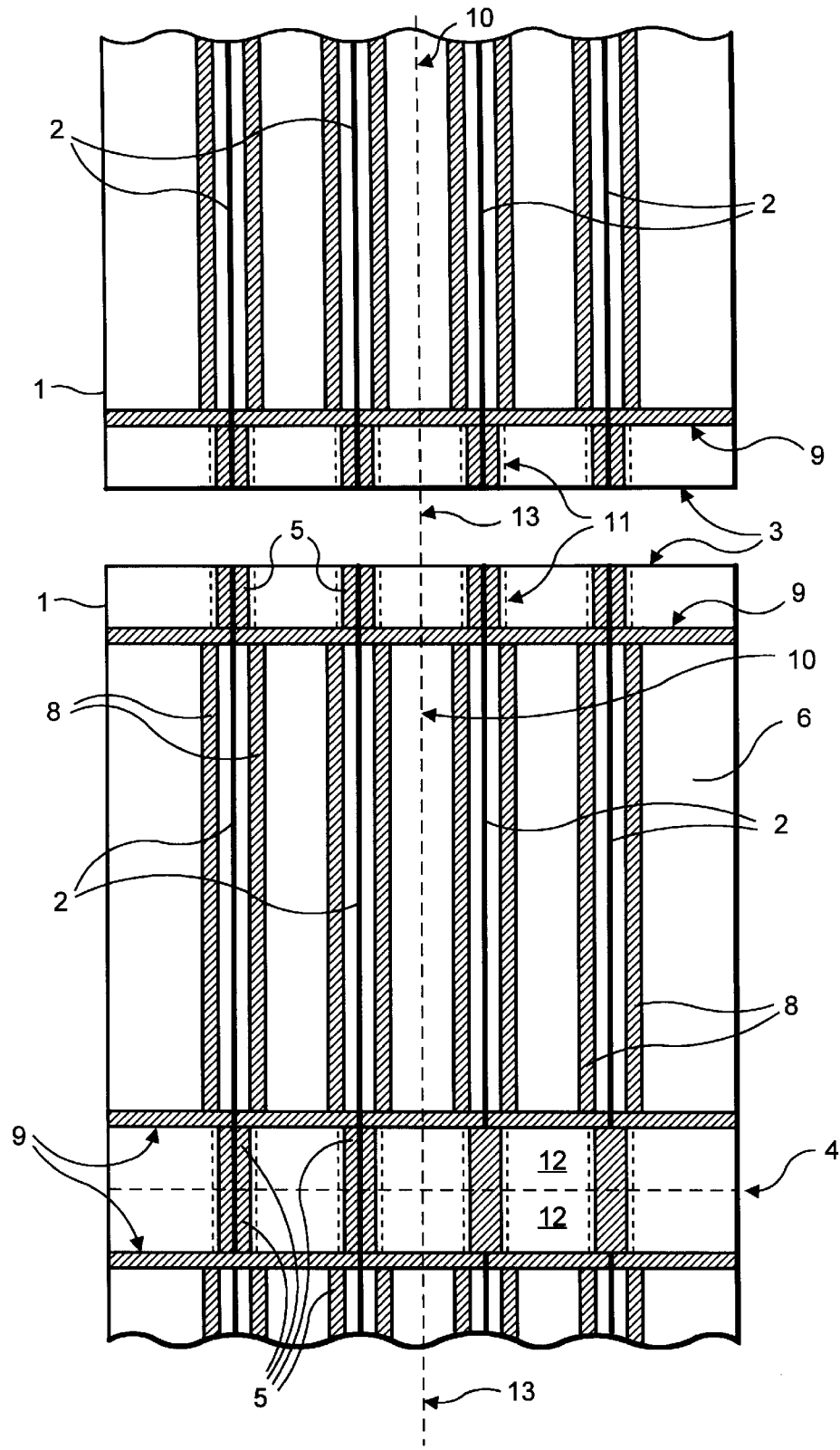
F I G. 1

STERILE DENTAL FLOSS SEGMENTS

This application is based on U.S. Provisional patent application No. 60/007,670, filed Nov. 28, 1995. The present invention relates generally to sterile dental floss segments having integral tips on the ends thereof, that are compatible for use in dental floss rings as disclosed in U.S. Pat. No. 5,435,330, or any similar type dental floss holder. The dental floss segments also have a predetermined length, and are enclosed in a laminated web matrix containing multiple strands of dental floss, which is designed to maintain the integrity of the sterility of the dental floss, even after one or more of the strands are removed for use, and in which the dental floss strands are sterilized. The present invention further relates to the method and apparatus to manufacture the sterile web units containing the sterilized dental floss segments with the integral tips on the ends.

BACKGROUND

With the increasing public awareness of the need for dental hygiene and teeth cleanliness, an increasing need has developed for instruments to aid in tooth cleaning. Accordingly there has been recent development in the area of dental hygiene devices which are dental floss holders designed to hold a measured length of dental floss sufficient for cleaning one's teeth. These holders may be used with much more dexterity than tensioning a length of floss between the user's two index fingers, which must then be extended into the user's mouth while positioning the floss and moving it between the teeth.

An example of such a device is the dental floss ring device described in my U.S. Pat. No. 5,435,330, issued Jul. 25, 1995. This device comprises two ring elements adapted to receive and retain a segment of dental floss, the dental floss ends being designed to engage retaining means on the ring elements. These ring elements as dental floss holders require that the dental floss used therewith have a predetermined length and some means on the ends of the dental floss by which the floss can be gripped in tension. Rather than tie a knot at the ends of the floss, which is time consuming, tedious, difficult for people with limited dexterity, and often results in inefficient use of floss, it is advantageous to have a bead or pre-formed tip on the ends of the floss.

There are now well-known methods for treating advancing lengths of thermal plastic filament material, such as dental floss, by heat and pressure steps. Some of these methods form crimps in the filament or roughen the surface, which are unsuitable for the present use since neither crimps or roughness will provide sufficient grip when the filament is tensioned in the ring holders. Another known method for providing tips on the end of dental is by injection molding the tips onto the floss. Besides being a relatively slow process, it is also wasteful as the resulting dental floss segments must be broken apart and are disposable. Moreover, the injection molded bead does not form a very strong bond with the dental floss and the floss is non-sterile.

Another disadvantage of dental floss is that it is not sterile. Generally, dental floss is sold in plastic, non-sterile containers in spool form. Even if the dental floss was initially sterilized, once the container is opened sterility cannot be maintained. Moreover, sterilized dental floss segments in predetermined lengths are not known.

Methods and apparatus such as that described in U.S. Pat. No. 3,843,297 form measured lengths of dental floss with nubs on both ends thereof by placing continuous lengths of dental floss between pairs of heat-resistant bars formed into a grid. Heat passing between the bars melts the exposed dental floss equal in length to the width of the bars with nubs formed integrally on the ends. This method is cumbersome in that it is not a continuous process amenable to rapid, large-scale production, and also does not provide for the sterile manufacture of the floss.

Known methods for manufacturing dental floss having beaded ends are inadequate for the present intended use. For example, a method for manufacturing dental floss having beaded ends is disclosed in U.S. Pat. No. 5,167,753. This method is directed to a process which imbeds a single stranded filament into slotted beads, which are then glued into place. In addition, U.S. Pat. No. 4,029,453, is directed to an apparatus which holds and tensions the dental floss while the dental floss holder is molded onto the ends of the floss itself. This type of method does not provide for a separate dental floss product independent of the holder, requiring the holder to be disposable along with the floss, unlike the present invention in which only the floss itself need be disposable. Neither of these known methods provide for a sterile dental floss product, nor are they amenable to mass production as in the present invention.

An object of the present invention is, therefore, to provide a dental floss product of predetermined length and having integral tips of the ends thereof that are compatible for use in dental floss holders.

It is a further object of the present invention to provide a packaged unit containing multiple strands of dental floss segments which allows for the sterilization of the strands within the unit and further maintains the integrity of the sterility of the dental floss as the individual strands are removed for use.

Another object of the present invention is to overcome the deficiencies in the known methods for manufacturing dental floss of a predetermined length and having beaded ends. The present invention provides a unique method and apparatus for manufacturing such dental floss segments which are compatible with dental floss holders, preferably the ring holder elements as identified above.

It is a further object of the present invention to provide a method and apparatus which sterilizes and maintains sterility of the resulting dental floss product, in the context of the manufacturing process and during use of the dental floss product.

It is a further object of the present invention to provide a method and apparatus which is readily adaptable to rapid production, providing for relative ease of manufacture and packaging, resulting in reduced costs over conventional methods.

SUMMARY

In the preferred embodiment, the present invention provides sterile dental floss segments of predetermined length in laminated package units containing multiple strands of dental floss. The dental floss segments each have integral tips on the ends, formed by the application of hot melt adhesive on the ends of the floss, which hardens as it cools thus forming the tips. The laminated units are constructed of either a sterilizable or sterilized FDA approved substrate, which are joined together, i.e., laminated, by hot melt adhesive as applied to one side of one of the substrates. The first substrate is then joined to the second substrate having the dental floss segments sandwiched inbetween. Further, the hot melt adhesive is applied to the first substrate such that, after joining with the second substrate, each dental floss segment is completely sealed within the substrates and the adhesive, by which sterility can be maintained. That is, any one of the dental floss segments may be removed from the laminated unit without disturbing the seal and sterility of any other dental floss segment. The laminated unit is further perforated so that sections may be detached for storage and travel, each detached section containing any multiple of dental floss segments. Once the laminated unit is constructed, the dental floss segments sealed inside, as well as the unit itself, is sterilized using an electron beam sterilization technique.

The present invention also provides a method and apparatus for manufacturing the sterile dental floss segments of predetermined length and having beaded ends. The dental floss segments are produced in sterile, laminated units by am uncomplicated hot melt adhesive application technique which is amenable to rapid and economical mass production.

Dental floss is first loaded from a source in continuous strand form onto a beam, from which it subsequently supplied in parallel strands in the form of a web, much like the web used on a loom for weaving. The web passes through a thread guide which precisely aligns and tensions the floss. As the web exits the thread guide, it then enters an oncoat laminating device which laminates two glassine substrates onto the strands of the web using a hot melt adhesive, one glassine substrate on each side of the web. The hot melt adhesive is applied to one side of the first glassine substrate, such that is parallel to and is one both sides of each strand of the dental floss, so that when the two substrates are joined joined in lamination, the hot melt adhesive seals the sides of each floss segment. Hot melt adhesive is also applied across the strands of the web at predetermined intervals, forming seals at the end of each floss segment and creating the beaded ends or tips on the floss.

As the web is cooled as it leaves the hot melt laminating station, causing the hot melt adhesive to rapidly harden. After cooling, the web is perforated lengthwise, again at predetermined intervals, between any specified number of strands by use of a perforator. The perforator also outlines the tips of the floss by perforating around the edges of the tips. The web is then cut across the section horizontally at specific intervals using a cutting device, separating the web into units. Prior to packaging, the laminated units of dental floss segments are sterilized using, preferably, electron beam sterilization, which leaves no residue The means for accomplishing the foregoing objects and other advantages of the present invention will be apparent to those skilled in the art and become clearer in light of the following detailed description of an illustrative embodiment of the present invention described in connection with the drawings.

BRIEF DESCRIPTION OF THE DRAWINGS

FIG. 1 is a top view of laminated, segmented dental floss units according to the invention.

DETAILED DESCRIPTION OF THE INVENTION

Figure 2:
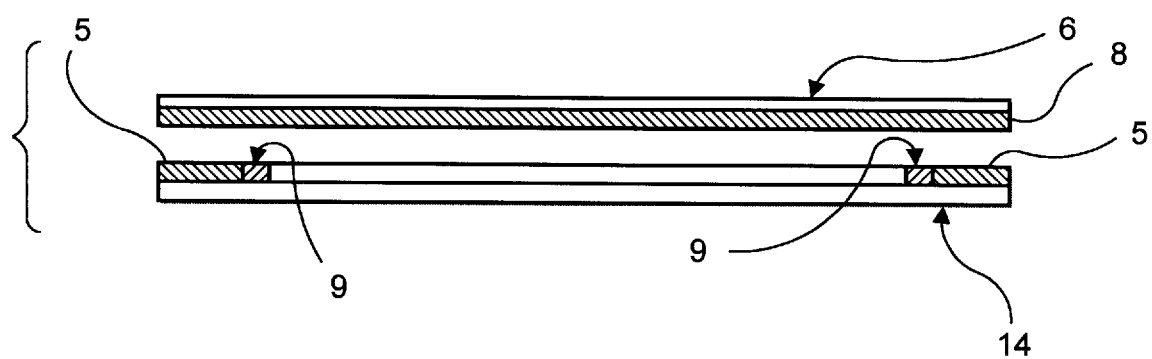
FIG. 2 is a horizontal view of the laminated units of FIG. 1.

The laminated units containing the sterile dental floss segments with beaded ends, as well as the method and apparatus for manufacturing them, are discussed with reference to the accompanying figures.

FIG. 1 shows a top view of laminated units 1 of the present invention, containing strands of dental floss 2. The two laminated units 1 are illustrated subsequent to being cut and separated from each other at point 3. The cuts separating each laminated unit are made across the laminated "web," as will be more completely described below. The web may have any desired width that can be accommodated by the manufacturing equipment, although it is presently preferred to have the web about 12 inches wide. It has been found that this width provides for lamination of a sufficient number of strands of dental floss.

The length of each individual laminated unit 1 is also variable, but is necessarily dictated by the length of dental floss needed for each individual use. Ideally, it has been determined that only about 4–5 inches of dental floss are needed per application by the user, so the cross cuts 3 on the laminated web are generally made at intervals of 4–5 inches.

As shown, each strand 2 of dental floss runs lengthwise through the laminated web until the web is cut 3 or perforated 4, dividing the strands into segments. Prior to separation of the strands into segments, adhesive is applied directly to the dental floss strands at predetermined intervals where it will become the integral beaded tips. When the adhesive cools, it solidifies, forming beads around the strands of dental floss. The adhesive can be any such adhesive that fulfills the requirements of the Code of Federal Regulations, Title 21, section 175.105, for food-packaging adhesives. Typically, the adhesives are cold adhesives, hot melt adhesives ("HMAs"), or polyamides as known to the paper cartoning and packaging industry, with HMAs being preferred. The adhesive may be applied in any thickness from about $\frac{1}{8}$ inches to about $\frac{1}{32}$ inches, with about a $\frac{1}{16}$ inches thickness being preferred.

The laminated units are formed by joining two layers of sterilizable substrate 6 (only the top layer is shown in FIG. 1), with the dental floss strands in between. The substrate may be any kind of material that is both sterilizable and waterproof. Materials such as coated papers, mylar and glassine HMA is applied to one side of one of the layers of substrate, which then bonds with the second substrate upon joining. In addition, the HMA is applied in such a manner that, when the laminated unit is formed, the dental floss segment is sealed having the HMA as the boundaries of the seal. As shown in FIG. 1, for example, HMA is applied in a lengthwise direction 8, in spaced apart fashion, for positioning the dental floss strands 2 in between the strips of HMA. Similarly, HMA is also applied to the substrate 6 running across the web at predetermined intervals, enclosing and sealing the "ends" of the dental floss strands 9.

The ends of the dental floss segments having the integral tips 5, however, can extend beyond the crosswise HMA since sterility need not be maintained at this point. The HMA can essentially be of any desired width, but it is advantageous to maintain as narrow a width as possible in order to allow as many strands as possible of dental floss to be sealed. Consequently, the width of the HMA is dictated by the capability of the machine making the HMA application. Widths of about $\frac{1}{32}$ inches of HMA are customarily achieved.

After laminating the web, the laminated unit is perforated lengthwise 10 for separation into smaller units. The perforations are not placed in between each sealed dental floss segment, but are spaced apart as desired such that any number of segments are contained in the separated smaller unit. For example, it is contemplated by the preferred embodiment that the lengthwise perforations be placed about 1 inch apart. Therefore, allowing for two rows of HMA per dental floss strand of ⅟₃₂ inches each, and allowing additional space for the floss strand itself, it can be seen that at least approximately 12 dental floss segments may be contained in a 1 inch wide laminated unit. It is also understood that, for each of these laminated units separated after perforation, one of the dental floss segments may be removed by grasping the end and tearing the strands from the laminate substrates. In so doing, the seals formed around the remaining segments will not be disturbed, thereby maintaining the integrity of the sterility of those segments. This is accomplished by additional perforations 11 being placed in the laminated unit around the extended tip of the dental floss segment. In an alternate embodiment, the laminate sections 12 may be entirely cut away, exposing the beaded tips which need not remain sterile since they are to be attached to the dental floss holder and not inserted into the mouth.

FIG. 2 shows a side view of a laminated unit in the direction of the axis 13. An upper or first sterilizable substrate 6 is shown having the HMA 8 previously applied to one side thereof, facing the lower or second sterilizable substrate 14. The substrates are shown spaced apart and prior to being laminated. The dental floss strand 2 is inbetween the substrates 6, 14, although it is not necessarily joined to the lower substrate 14. At the ends of the floss strand 2 are the integral tips 5 formed by the HMA. A cross-sectional view of the crosswise application of HMA 9 is also seen.

Figure 3:
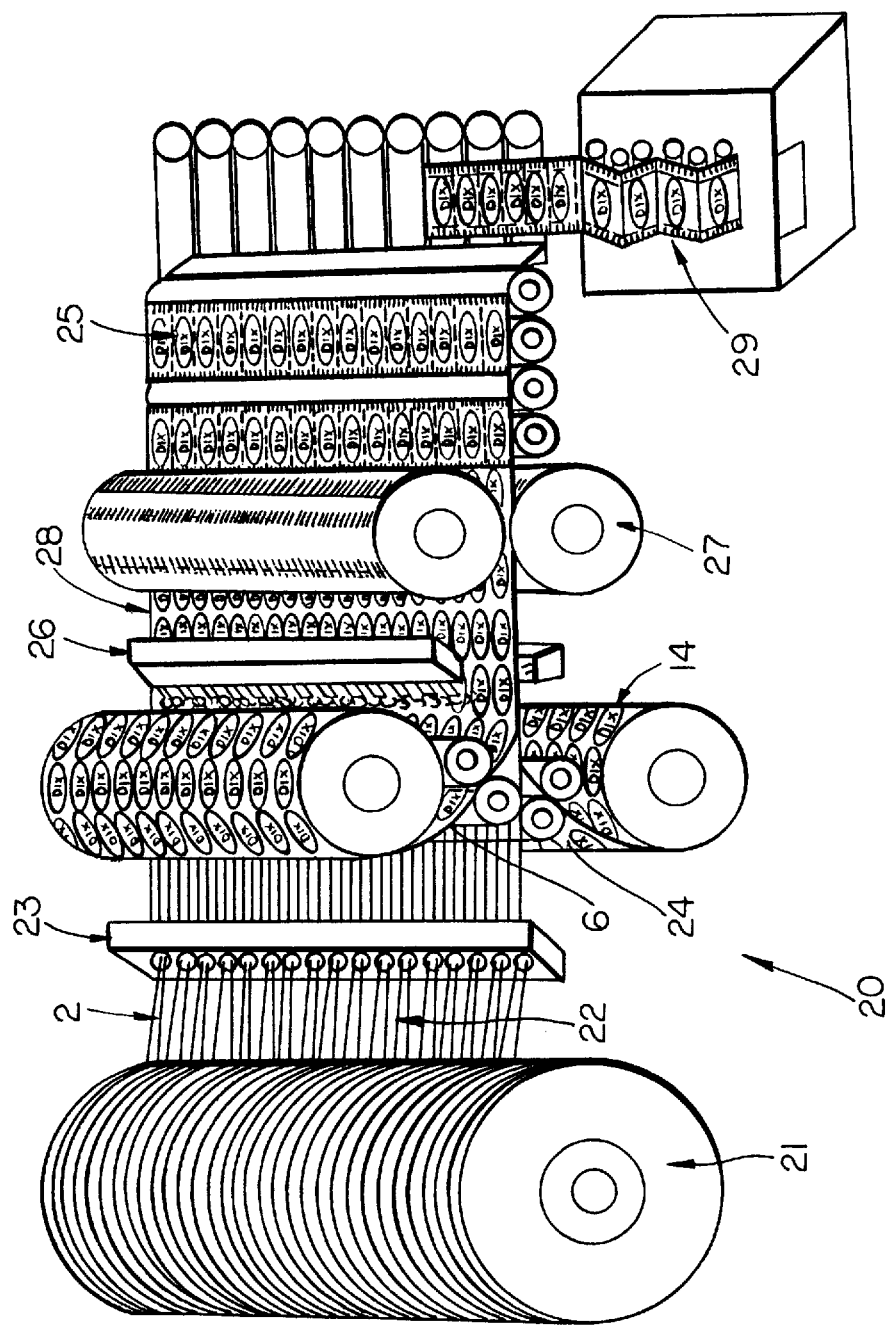
FIG. 3 is a plan view of the apparatus for making the sterile, segmented dental floss with beaded ends.

In FIG. 3, the apparatus for performing the process steps for manufacturing the sterile, segmented dental floss units is shown generally 20. In the first part of the process, dental floss in the form of a single strand is loaded from a source holder (not shown), onto beam 21 in parallel fashion. The type of beams used are textile beams or loom beams as known in the textile industry. Examples of such beams are section beams, loom beams, tricot beams and raschel beams. From the beam 21, the dental floss 2 is continuously inputted into the apparatus as it is unwound in the parallel manner it was loaded, with each strand next to each other, forming a web 22. In conventional dental floss processes, the dental floss is generally cross-wound onto a spool, from which it is supplied as a continuous, single strand. The web 22 formed by the present invention is similar in structure as the web formed in a loom for weaving.

As the web 22 leaves the beam 21, it passes a thread guide 23 which precisely aligns and tensions the floss for the next step in the process, which is lamination. The thread guide used may be any one known in the textile industry that will provide the required result. Exiting the thread guide 23, the dental floss strands are precisely parallel and spaced apart at any desired distance, taking into account the space needed between the strands for the hot melt adhesive. In the preferred embodiment, the resultant laminated unit 25 is about 12 inches wide and contains from about 90 to about 150 strands of dental floss segments. The tension supplied should be sufficient to firmly hold the dental floss strands while not allowing them to be stretched.

Once aligned and tensioned, the web 22 is ready for the lamination process, which applies the HMA to the dental floss strands and to one side of the sterilizable substrate 6, in addition to enclosing and sealing the floss web. These operations are conducted relatively simultaneously by use of a hot melt laminating unit 24. In the laminating unit 24, the web 22 becomes married between two sterilizable glassine substrates using hot melt adhesive. See FIG. 2. In this stage of the operation, HMA is applied to one of the glassine substrates 6 in a pattern which surrounds each individual strand of the web 22, coating the substrate inbetween each strand of floss. The laminating unit 24 also applies the HMA to the dental floss strands at predetermined intervals, which will eventually become the integral tips on the ends of the floss segments after the strands are cut. The HMA is applied in strips of about ½ inches in width, perpendicularly across the entire web. The intervals are selected according to the desired length of the final floss segment, but ideally it has been determined that 4 to 5 inch intervals provide an adequate amount of floss. In applying the strips of HMA, a thickness of about ⅟₁₆ inches is maintained to ensure an adequate bead for attachment with the dental floss holder. When die-cut according to a later stage of the process, the resulting floss tips are approximately ¼ by ⅟₁₆ inches. Alternatively, the HMA may be applied to form beads in a back-to-back pin type configuration. When cut, the resulting tip is in the form of a bead, much like the head of a pin.

In addition, the laminating unit 24 applies the HMA crosswise on the substrate 6 at predetermined intervals to form the end closures of the floss segments. FIG. 2, at 9. The glassine substrate 6 with the HMA is then "married" with the second glassine substrate 14, laminating the strands of the web. Thus, each dental floss strand of the web becomes sealed, ensuring the integrity of the sterilization process, which is performed later on the completed laminated units 25.

The apparatus selected for the HMA application/laminating process may be of the type used in the paper industry as used in the coating and laminating of paper products, as well as the manufacture of products such as corrugated cardboard. These machines generally are individually designed to specifications dictated by the contemplated use, and generally comprise an adhesive application system, including a source of HMA, and a laminating system. Companies such as ITW Dynatec manufacture these machines.

As the web 22 travels from the hot melt laminating unit 24, it is cooled causing the HMA to harden rapidly. This can be accomplished by using cooling jets 26, a chilled conveyer belt or any other method or device consistent with the overall process that produces the desired result. The cooling of the web 22 gives it the structural strength to pass through the next stage of the process, which is perforation and die-cutting.

After the web is cooled, it next enters a perforator/die cutting device 27 where the now laminated web 28 is perforated lengthwise at widths of approximately 1 inch. This operation is performed through the use of a rotary die cutter/perforating roll, which outlines the tips of the floss segments and determines the width of the package. The tips of the floss segments are outlined by perforating around the edges of the tips, allowing the consumer to pull out a dental floss segment by breaking the laminate around the tip and pulling out the floss segment, leaving the sterility of the remaining segments intact. The laminated web 28 is then cut across the section of the web horizontally at approximately 4–5 inch intervals, separating the laminated web 28 into laminated units 25. As shown in FIG. 3, both perforation and die cutting are performed in a single operation using the rotary die cutter/perforator roll. However, other methods and apparatus will be apparent to those of skill in the art. For example, the perforation could be performed separately from the die cutting.

After the laminated web 28 is die-cut and perforated, the laminated units 25 are approximately 12 inches in width and 4–5 inches in length. These units 25 can be fed into a folding station 29 where the laminated unit 25 is folded accordion-style at approximately three inch intervals. The folded laminated units may then be fed into a mylar bagging device, where they are sealed in a mylar pouch similar to a pack of baseball cards.

Once the laminated units are sealed in the mylar bags, the floss segments can be sterilized. The process of manufacturing each floss segment individually sealed with HMA allows for the integrity of a sterilization procedure to be performed and maintained. This is conducted in a batch process through the mylar packaging in similar fashion as the procedure for sterilizing sutures. The preferred sterilization method is Electron Beam Sterilization ("EBS"), which leaves no residue and renders the floss segments and the sterilizable substrate sterile. Due to the nature of technological advances, other methods of sterilization may prove to be more efficient, so the process need not be limited to EBS as the sole method.

The present invention may be embodied in other specific forms without departing from the spirit or essential characteristics thereof. The present embodiment is therefore to be considered in all respects as illustrative and not restrictive, the scope of the invention being indicated by the appended claims rather than the foregoing description and all changes which come within the meaning and range of equivalency of the claims are therefore to be embraced therein.

What is claimed is:

1. A laminated unit containing sterile segments of dental floss, comprising:

a plurality of sterile dental floss segments having predetermined lengths, each dental floss segment comprising a strand of dental floss having a hardened, integral tip on each end, each said tip being configured for being insertable into a holder designed to accept said integral tip, a first sterilizable substrate, a second sterilizable substrate, and an adhesive, wherein the first sterilizable substrate is joined to the second sterilizable substrate, with the dental floss segments positioned therebetween, by use of the adhesive, to form a laminated unit wherein the adhesive and the first and second sterilizable substrates entirely enclose each separate dental floss segment and form a seal which is capable of maintaining sterility of the dental floss segment within, and wherein said hardened, integral tip is formed from said adhesive.

2. The laminated unit according to claim 1, wherein the laminated unit and the dental floss segments contained therein are sterilized, said sterilization taking place after formation of the laminated unit.

3. The laminated unit according to claim 1, wherein the integral tips on the ends of each dental floss segment are formed from the adhesive having been applied onto the dental floss segment and then hardened.

4. The laminated unit according to claim 3, wherein the adhesive is an FDA approved adhesive selected from the group consisting of cold adhesives, hot melt adhesives and polyamides.

5. The laminated unit according to claim 4, wherein the adhesive is a hot melt adhesive.

6. A The laminated unit according to claim 5, wherein the hot melt adhesive has a thickness from about 1/32 inches to about 1/8 inches.

7. The laminated unit according to claim 6, wherein the hot melt adhesive has a thickness of about 1/16 inches.

8. The laminated unit according to claim 3, wherein the integral tips are compatible for removable attachment with dental floss holders.

9. The laminated unit according to claim 1, wherein the first and second sterilizable substrates are selected from the group consisting of coated paper, glassine, presterilized glassine and mylar.

10. The laminated unit according to claim 9, wherein the first and second sterilizable substrates are glassine.

11. The laminated unit according to claim 1, wherein the dental floss segments are arranged substantially parallel to one another.

12. The laminated unit according to claim 1, wherein the predetermined length of the dental floss segments is from about 4 inches to about 5 inches.

13. A dental floss segment having a predetermined length and integral tips on the ends thereof being configured for removable attachment with a dental floss holder wherein the integral tips comprise an adhesive which has been applied to the dental floss ends and allowed to harden.

14. The dental floss segment according to claim 13, wherein the adhesive is selected from the group consisting of cold adhesives, hot melt adhesives and polyamides.

15. The dental floss segment according to claim 14, wherein the adhesive is a hot melt adhesive.

16. The dental floss segment according to claim 13, wherein the dental floss segment is sterilized.

17. The dental floss segment according to claim 16, wherein the sterilized dental floss segment is sealed in a laminated enclosure comprising a first and second sterilizable substrate and adhesive.

18. The dental floss segment according to claim 17, wherein the first and second sterilizable substrates are glassine.

* * * * *